(12) United States Patent
Wickert et al.

(10) Patent No.: US 6,900,028 B2
(45) Date of Patent: May 31, 2005

(54) REFLECTIVE DISC ASSAY DEVICES, SYSTEMS AND METHODS

(75) Inventors: Peter D. Wickert, St. Paul, MN (US); Michael G. Williams, Vadnais Heights, MN (US); Christine A. Binsfeld, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 243 days.

(21) Appl. No.: 10/268,654

(22) Filed: Oct. 10, 2002

(65) Prior Publication Data

US 2003/0040034 A1 Feb. 27, 2003

Related U.S. Application Data

(62) Division of application No. 09/562,832, filed on May 1, 2000, now Pat. No. 6,492,133.

(51) Int. Cl.[7] .............................................. C12Q 1/02
(52) U.S. Cl. .................. 435/29; 435/34; 435/287.4; 435/287.7; 435/287.8; 435/288.3; 435/288.7
(58) Field of Search .................. 422/56, 61; 435/287.1, 435/287.4, 287.7, 287.8, 288.3, 288.7, 4, 29, 34

(56) References Cited

U.S. PATENT DOCUMENTS

| | | | |
|---|---|---|---|
| 3,853,467 A | 12/1974 | Giaever | |
| 3,926,564 A | 12/1975 | Giaever | |
| 3,979,509 A | 9/1976 | Giaever | |
| 4,266,108 A | 5/1981 | Anderson et al. | |
| 4,387,156 A | 6/1983 | Crawford et al. | |
| 4,390,343 A | 6/1983 | Walter | |
| 4,649,280 A | 3/1987 | Holland et al. | |
| 4,820,649 A | 4/1989 | Kawaguchi et al. | |
| 4,985,300 A | 1/1991 | Huang | |
| 5,192,502 A | 3/1993 | Attridge et al. | |
| 5,278,377 A | 1/1994 | Tsai | |
| 5,317,045 A | 5/1994 | Clark, Jr. et al. | |
| 5,446,270 A | 8/1995 | Chamberlain et al. | |
| 5,482,830 A | 1/1996 | Bogart et al. | |
| 5,529,708 A | 6/1996 | Palmgren et al. | |
| 5,541,057 A | 7/1996 | Bogart et al. | |
| 5,734,587 A | 3/1998 | Backhaus et al. | |
| 5,830,766 A | 11/1998 | Attridge et al. | |
| 5,869,001 A * | 2/1999 | Backhaus et al. | 422/58 |
| 5,869,272 A | 2/1999 | Bogart et al. | |
| 5,910,287 A | 6/1999 | Cassin et al. | |
| 5,916,203 A | 6/1999 | Brandon et al. | |
| 5,925,455 A | 7/1999 | Bruzzone et al. | |
| 6,395,483 B1 | 5/2002 | Patil et al. | |

FOREIGN PATENT DOCUMENTS

| | | |
|---|---|---|
| EP | 0 333 253 | 9/1989 |
| GB | 2 065 298 A | 6/1981 |
| WO | WO 99/53319 A3 | 10/1999 |
| WO | WO 99/53319 A2 | 10/1999 |

* cited by examiner

Primary Examiner—David A. Redding
(74) Attorney, Agent, or Firm—Daniel R. Pastirik

(57) ABSTRACT

Disc assay devices and methods for the detection and enumeration of microorganisms are disclosed. The devices and methods include a plurality of discs attached to a substrate and a reflector on one surface of each of the discs to reflect electromagnetic energy of selected wavelengths after the energy has passed through the disc. The reflector may be useful to improve the accuracy of detection and/or enumeration of target microorganisms on the assay devices. A system for detecting and/or enumerating target microorganisms on disc assay devices is also provided.

9 Claims, 3 Drawing Sheets

REFLECTIVE DISC ASSAY DEVICES, SYSTEMS AND METHODS

Related Applications

This application is a divisional of U.S. Ser. No. 09/562,832 filed May 1, 2002, now U.S. Pat. No. 6,492,133.

FIELD

This invention relates to disc assay devices, systems, and methods of use for culturing biological samples to detect and/or enumerate microorganisms present within the samples.

BACKGROUND

The detection and enumeration of microorganisms is practiced in numerous settings, including the food-processing industry (testing for the contamination of food by microorganisms such as *E. coli* and *S. aureus*), the health care industry (testing of patient samples and other clinical samples for infection or contamination), environmental testing industry, the pharmaceutical industry, and the cosmetic industry.

Growth-based detection and enumeration of microorganisms is commonly practiced using either liquid nutrient media (most probable number analysis (MPN)) or semi-solid nutrient media (agar petri dishes). Enumeration using the liquid MPN method is typically achieved by placing serial 10-fold dilutions of a sample of interest in replicate sets of tubes containing selective media and chemical indicators. The tubes are incubated at elevated temperature (24–48 hours) followed by examination for growth of organisms. A statistical formula, based on the volume of sample tested and the number of positive and negative tubes for each set, is used to estimate the number of organisms present in the initial sample.

This method of performing MPN analysis has several disadvantages. It is labor intensive because of the multiple diluting and pipetting steps necessary to perform the analysis. In addition, in practice it is only practical to use replicate sets of about three to five tubes for each dilution. As a result, the 95% confidence limits for an MPN estimate for microbial concentration are extremely wide. For example, a three tube MPN estimate of 20 has 95% confidence limits ranging from 7 to 89.

In contrast to the method described above, a direct count of viable microorganisms in a sample can be achieved by spreading the sample over a defined area using nutrient media containing a gelling agent. The gelling agent (agar) prevents diffusion of the organisms during incubation (24–48 hours), producing a colony in the area where the original organism was deposited. There is, however, a limit to the number of colonies that can fit on a given area of nutrient media before fusion with neighboring colonies makes counting difficult. This usually necessitates performing several dilutions for each sample. In addition, the classes of chemical indicator molecules that can be used for identifying individual types of microorganisms present within a mixed population are limited to those that produce a product that is insoluble in the gelled media.

In some of these processes, the detection or enumeration of a microorganism is determined by detecting an electromagnetic signal, e.g., fluorescence, emitted by an indicator substance in response to excitation (where the indicator substance is activated by presence of the microorganism to be detected). The excitation may be provided in the form of electromagnetic energy from, e.g., a laser. One potential problem with known assay devices is that the electromagnetic energy used for excitation may also excite other materials present in the substrate or other portions of the device, causing them to emit an electromagnetic signal similar to that emitted by the desired indicator. For example, where the assay is formed on a polymeric substrate that fluoresces in the same or similar wavelength regions as the indicator, a relatively high background electromagnetic signal can be produced by the substrate that reduces the signal-to-background ratio. A lower signal-to-background ratio can make accurate detection or enumeration of the desired microorganism more difficult.

SUMMARY

The invention provides devices and methods for the detection and enumeration of microorganisms. The devices and methods include a plurality of discs attached to a substrate and a reflector proximate one surface of each of the discs to reflect electromagnetic energy of selected wavelengths after the energy has passed through the disc. The reflector may be useful to improve the accuracy of detection and/or enumeration of target microorganisms on the assay devices. A system for detecting and/or enumerating target microorganisms on disc assay devices is also provided.

One advantage of the devices and methods of the present invention is that the reflectors proximate each of the discs may reflect the excitation energy directed at the discs after it has passed through the discs. As a result, the effective path length of the excitation energy through the discs is doubled as compared to assay devices in which the excitation energy is not reflected after passing through the discs. That increased path length may improve the accuracy of the detection and/or enumeration of microorganisms by effectively increasing the intensity of the excitation energy.

Another potential advantage of the devices and methods of the invention is that the reflectors may improve the signal-to-background ratio during detection and/or enumeration of target microorganisms. In some instances, the reflectors preferably reduce or prevent transmission of the excitation energy to the underlying substrate. In other instances, the reflectors may reduce or prevent the transmission of electromagnetic energy from, e.g., the substrate, that is similar to the electromagnetic signal energy emitted by, e.g., an indicator substance, in response to the excitation energy. In either case, with the reflectors in place, the electromagnetic signal energy emitted from the assay device may more accurately indicate the presence of the target microorganisms, rather than the underlying substrate or other portions of the device.

The signal-to-background ratio may be further improved if the reflectors are also reflective for the electromagnetic signal energy generated as a result of the presence of the target microorganisms within or on the discs. If the reflectors are located on the side of the discs opposite the detector, at least a portion of the electromagnetic signal energy that is emitted in the direction of the reflectors may be reflected back towards the detector, thereby potentially increasing the intensity of the emitted signal energy. Increases in emitted signal energy intensity may improve detection accuracy and, in some instances, may also allow for detection of the target microorganisms after shorter incubation periods.

With respect to the excitation/detection systems of the present invention which include reflective walls, one potential advantage is that the reflectivity of the walls may improve uniformity in excitation of the assay devices being sampled.

In one aspect, the present invention provides a microorganism culture device including a substrate; a plurality of liquid-retaining discs attached to the substrate, wherein each of the plurality of discs has first and second opposing surfaces; and a reflector proximate the first surface of each of the plurality of discs, wherein electromagnetic energy of selected wavelengths is reflected from the reflector after passing through the disc.

In another aspect, the present invention provides a method of detecting at least one target microorganism by providing a disc assay device including a substrate; a plurality of liquid-retaining discs attached to the substrate, each of the plurality of discs having first and second opposing surfaces; and a reflector proximate the first surface of each of the plurality of discs; and wherein at least one of the discs further includes growth media, an indicator substance, and a target microorganism; directing excitation energy at the disc assay device; and detecting signal energy emitted from each of the plurality of discs including the target microorganism in response to the excitation energy; wherein at least a portion of the signal energy is reflected by the reflector.

In another aspect, the present invention provides a method of manufacturing a disc assay device by providing a substrate; locating a plurality of liquid-retaining discs on the substrate, each of the plurality of discs having first and second opposing surfaces; and providing a reflector proximate the first surface of each of the plurality of discs, wherein electromagnetic energy of selected wavelengths is reflected from the reflector after passing through the disc.

In another aspect, the present invention provides a system for detecting target microorganisms on a disc assay device, the system including at least one excitation source emitting electromagnetic excitation energy of selected wavelengths; a detection chamber including at least one wall, wherein the at least one wall reflects a significant portion of the electromagnetic excitation energy incident thereon; and a detector arranged within the detection chamber to detect electromagnetic signal energy emitted from the assay device in response to the electromagnetic excitation energy.

These and other features and advantages of the invention will be described in connection with illustrative embodiments of the invention below.

As used herein, the term "microorganism" includes all microscopic living organisms and cells, including without limitation bacteria, mycoplasmas, rickettsias, spirochetes, yeasts, molds, protozoans, as well as microscopic forms of eukaryotic cells, for example single cells (cultured or derived directly from a tissue or organ) or small clumps of cells. Microorganisms are detected and/or enumerated not only when whole cells are detected directly, but also when such cells are detected indirectly, such as through detection or quantitation of cell fragments, cell-derived biological molecules, or cell by-products.

DESCRIPTION OF ILLUSTRATIVE EMBODIMENTS OF THE INVENTION

The invention provides devices and methods for the detection and/or enumeration of target microorganisms. The devices and methods include a plurality of discs attached to a substrate and a reflector proximate one surface of each of the discs to reflect electromagnetic energy of selected wavelengths after the energy has passed through the disc. The reflector may be useful to improve the accuracy of detection and/or enumeration of target microorganisms on the assay devices. A system for detecting and/or enumerating target microorganisms on disc assay devices is also provided. Illustrative embodiments of these different aspects of the invention are described below.

The assay devices and methods of the present invention include a plurality of liquid-retaining discs on a substrate. Where the present invention recites "each of the plurality of discs," it will be understood that one or more other discs may be included on the assay device that do not possess that characteristic.

Examples of some assay devices are described in commonly-assigned and co-pending U.S. patent application Ser. Nos. 08/838,397, filed Apr. 9, 1997 (International Publication No. WO 98/45406); 08/997,337, filed Dec. 23, 1997 (International Publication No. WO 99/32601); and 09/264,804, filed Mar. 9, 1999.

One particularly useful application of the devices and methods of the invention is in the growth-based detection and enumeration of microorganisms in liquid test samples. Such growth-based detection and enumeration is very important in the testing of food, environmental, clinical, pharmaceutical, cosmetic, and other samples for contamination by microorganisms. The methods and devices of this invention allow for the efficient, accurate, convenient, and cost-effective testing of such samples. One preferred use of the methods and devices of this invention in such microbiological testing may be in Most Probable Number (MPN) analysis.

Figure 1:
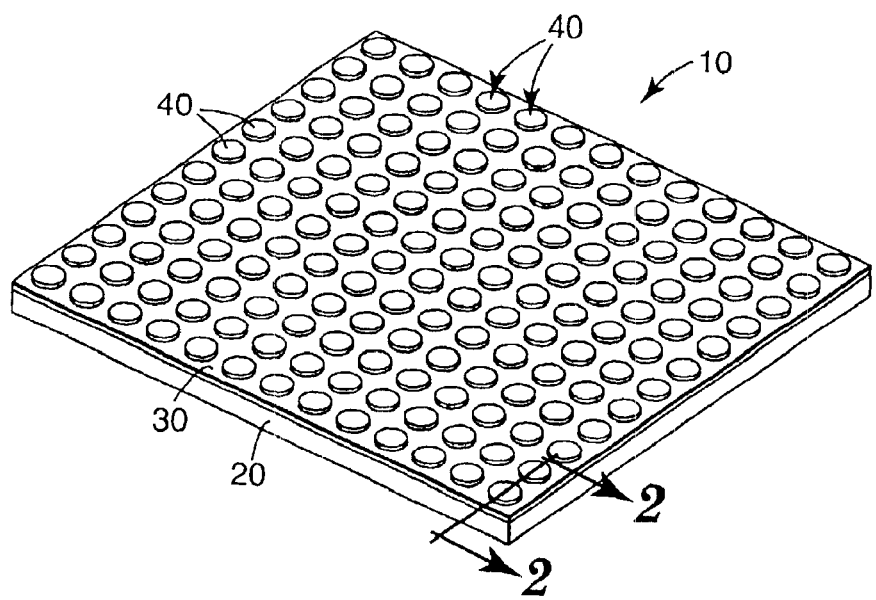
FIG. 1 is a perspective view of one embodiment of an assay device according to the present invention.
Figure 2:
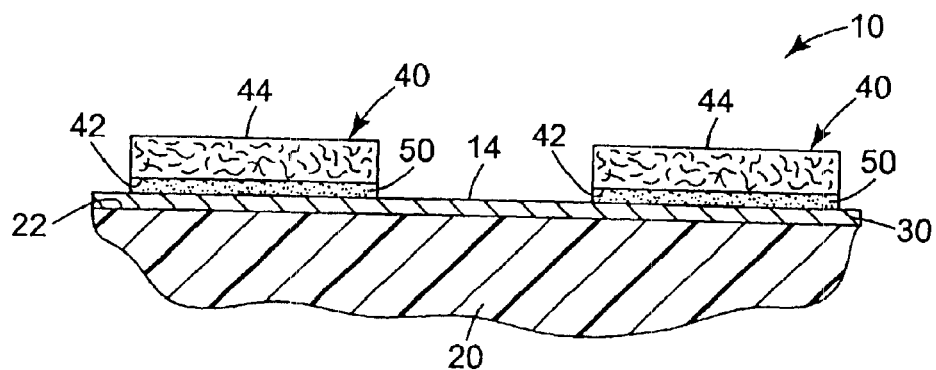
FIG. 2 is an enlarged partial cross-sectional view of the assay device of FIG. 1, taken along line 2—2 in FIG. 1.

With reference to FIGS. 1 and 2, one assay device 10 is illustrated. The substrate 20 of the assay device 10 defines a substrate surface 22 that provides suitable support for the discs 40 attached to the substrate 20 as described below. Although the substrates described in connection with the illustrative embodiments are generally planar films, the substrate 20 may take on any suitable shape provided that a surface of the substrate can provide the support required for the plurality of discs used in the assay device. It may be preferred that the portions of the assay device 10 other than the discs 40 be relatively hydrophobic to assist in preventing cross-contamination between the discs 40.

Substrate 20 can be fabricated, for example, from polymeric films or other appropriate materials. Appropriate polymers include without limitation polyethylene, polypropylene, polyester, polyimides, fluoropolymers, polycarbonates, polyurethanes, and polystyrenes. Preferably, the materials used for the substrate 20 will not leach any chemicals that may interfere with the growth or detection of target microorganisms. Although the substrate 20 is depicted as a single, homogeneous layer, it may be formed of two or more different materials provided in layers or otherwise. Alternatively, the substrate 20 may be formed of multiple layers of the same material.

The discs 40 attached to substrate 20 include first and second opposing surfaces 42 and 44 that in the illustrative embodiment are generally planar. Generally, the surface 42 facing the substrate 20 will have a shape that is complementary to the shape of the substrate surface to which the disc 40 is attached.

Although the discs 40 are illustrated as having a generally circular cylindrical shape, discs used in connection with the present invention can take any suitable shape and the present invention is not to be limited to circular cylindrically-shaped discs. For example, the discs may be of circular, oval, square, or polygonal shape or other appropriate shapes.

The discs 40 are preferably spaced apart from each other on the substrate surface 22 by a sufficient distance to prevent cross-contamination between the discs 40 during culturing. The area between the discs 40 will be referred to herein as the land area 14. The exact spacing between discs 40 will depend on a variety of factors that may include, but not limited to, the hydrophobicity of the substrate 20, the hydrophilicity of the discs 40, the nature of the sample being cultured, etc.

The discs 40 may be attached to the substrate 20 by various techniques known in the art, including without limitation, an adhesive 50 as illustrated in FIG. 2. For purposes of the present invention, the discs 40 are described as "attached to" the substrate 20 even though various materials, structures, etc. may be interposed between the discs 40 and the substrate 20. For example, the adhesive 50 is interposed between the discs 40 and the substrate 20. Preferred adhesives may include, e.g., water-insoluble isooctyl acrylate adhesives as disclosed in U.S. Pat. No. 5,409,838. The adhesive 50 may be provided alone or it may be provided on a scrim or other supporting layer in form of, e.g., a two-sided pressure sensitive adhesive tape.

The assay device 10 also includes a reflector 30 proximate the surface 42 of the discs 40 and the substrate 20. The reflector 30 reflects electromagnetic energy of selected wavelengths after that energy passes through the discs 40. By "reflect" (and its variations), it is meant that the reflector 30 substantially reduces or prevents transmission of the selected wavelengths of electromagnetic radiation. In preferred embodiments, the reflector 30 will reflect substantially all electromagnetic radiation of at least some selected wavelengths. The reduction in transmission should be significant enough to effectively increase the signal-to-background ratio provided by the resulting assay device.

The reflector 30 may, in some instances, transmit electromagnetic energy outside of the selected wavelengths. For example, the reflector 30 may exhibit an opacity for excitation energy wavelengths that is sufficiently high such that little or none of the excitation energy passes through the reflector 30 to the substrate 20. As a result, the excitation energy is substantially prevented from exciting materials in the substrate 20.

It may be preferred that the reflector 30 reflect a significant portion or substantially all of the wavelengths of the excitation energy and/or the electromagnetic signal energy. If the reflector 30 is reflective for the excitation energy, the effective path length of the excitation energy through the discs 40 can be effectively doubled as the excitation energy is reflected back through the discs 40 a second time after reflection from the reflector 30.

If the reflector 30 is reflective for the electromagnetic signal energy generated as a result of the presence of the target microorganisms within or on the discs 40, then any such signal energy that is emitted in the direction of the substrate 20 can be reflected, thereby increasing the chance that the emitted signal energy can be detected by a detector located above the second surface 44 of the disc 40.

The reflector 30 proximate the surface 42 of each of the discs 40 may take a variety of different forms. Regardless, however, it may be preferred that the reflector 30 not leach any chemicals that may interfere with the growth or detection of target microorganisms.

In one embodiment, the reflector 30 proximate the surface 42 of each of the discs 40 may be provided in the form of a reflective layer that reflects electromagnetic energy of selected wavelengths. The reflective layer may be constructed of any material, provided that it reflects the desired electromagnetic energy. For example, the reflective layer may be provided in the form of a metallic layer to provide the reflectors 30. The metallic layer may be formed by any known techniques for depositing metals on substrates, e.g., vapor deposition, sputtering, etc. Alternatively, any other suitable technique for providing a metallic layer with sufficient reflectivity for electromagnetic energy of selected wavelengths may be used. For example, a metallic layer may be provided in the form of a metal-containing matrix.

A metallic layer may include one or more metals, one or more metallic compounds, or combinations of one or more metals and one or more metallic compounds. Examples of suitable metals for a metallic layer may include, but are not limited to, aluminum, titanium, chromium, tin, gold, iron, platinum, palladium, silver, and combinations of two or more thereof. Metallic compounds may also be used to form a metallic layer. For example, the metallic layer forming the reflector 30 may include one or more metallic oxides, e.g., titanium dioxide, either in place of metals or in addition to metals. In some instances, it may be preferred that the metallic layer of reflector 30 consist essentially of one or more metals, one or more metallic compounds, or combinations of one or more metals and one or more metallic compounds.

Another alternative for the metallic layer of reflector 30 is that it may include one or more inks. It may be preferred that the ink be in the form of a curable ink, e.g., an ultraviolet curable ink such as a 100% solids ink. The ink or inks used in the reflector 30 may include pigments, dyes, synthetic resins, or any combination of these or other materials provided that the desired wavelengths of light are reflected. If the ink includes dyes, they are preferably non-fluorescent or fluorescent at wavelengths that do not interfere with the assay wavelengths relied on to detect the presence of the selected microorganisms.

Where a reflective layer is used to provide the reflectors 30 proximate the surfaces 42 of the discs 40 and that reflective layer is located on the substrate 20, the reflective layer may be substantially coextensive with the substrate surface 22 as illustrated in FIGS. 1 and 2. Alternatively, the reflective layer may be present on only portions of the substrate 20. At a minimum, however, a reflector 30 is provided proximate the surface 42 of each of the discs 40.

Figure 3A:
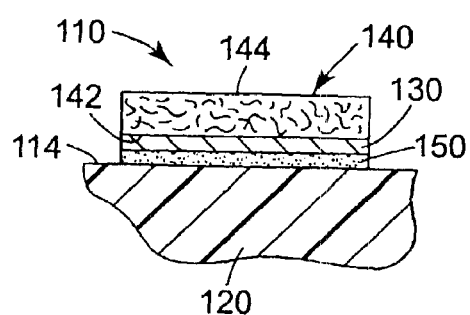
FIGS. 3A and 3B are cross-sectional views of alternative assay devices according to the present invention.

Referring to FIG. 3A, an assay device 110 is illustrated in which a reflector 130 is located only between the disc 140 and the substrate 120. The land areas 114 between adjacent discs 140 may preferably be substantially free of any reflector 130.

Another feature illustrated in the embodiment of FIG. 3A is the location of the reflector 130 directly on the surface 142 of disc 140 rather than on the substrate (as seen in the embodiment of FIGS. 1 and 2). The reflector 130 and disc 140 may be attached to the substrate 120 using, e.g., an adhesive 150 or any other suitable technique.

Figure 3B:
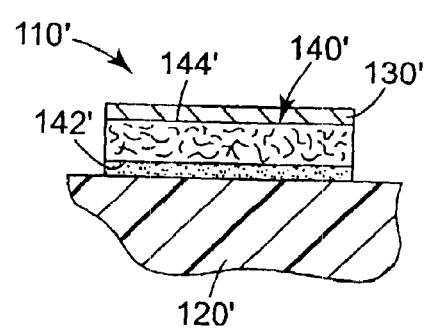

Referring to FIG. 3B, another assay device 110' is illustrated in which a reflector 130' is attached proximate the surface 144' that faces away from the substrate 120'. In such an embodiment, the disc 140' may be excited and read through the substrate 120', with the reflector 130' preferably reflecting electromagnetic signal energy traveling towards the surface 144' of the disc 140' back towards surface 142' and the substrate 120'. The reflector 130' also preferably reflects the excitation energy incident thereon such that the effective path length of the excitation energy through the disc 140' can be increased. In this embodiment, it may also be preferred that the substrate 120' be constructed of materials that do not substantially interfere with excitation and/or detection.

The liquid-retaining discs used in the assay devices of the invention may be constructed from a variety of materials. It may be preferred that at least a portion of the materials used in the discs be relatively hydrophilic. Alternatively, it may be preferred that the structure of the discs be such that liquid can be retained within the discs by, e.g., capillary wicking forces, etc. In such constructions, the materials used in the discs may or may not be hydrophilic.

The materials used in the discs may be fibrous, i.e., formed of a plurality of fibers, and the fibers may be woven or nonwoven to form the disc material. The disc materials may include, but are not limited to, cellulosics, polyolefins, polyesters, polyamides, etc. Suitable cellulosics may include paper, wood pulp and rayon and may include chemically modified cellulosics, such as cellulose esters. Suitable polyolefins may include hydrophilic polyethylene or hydrophilic polypropylene fibers. Suitable polyamides may include nylon. Suitable polyesters may include polylactic acid.

It may further be preferred that the materials used for the discs transmit a significant portion of both any electromagnetic excitation energy and electromagnetic signal energy. Both forms of energy may, however, experience some refraction or other diffusion when passing through the discs, particularly if the discs are formed of a fibrous material.

The thickness of the discs (as measured, e.g., between surfaces 42 and 44 in FIG. 2) may vary based on a variety of factors. It may, however, be preferred that the discs have a thickness of at least about 0.1 millimeter or more, more preferably at least about 0.3 millimeter or more. At the upper end, it may be preferred that the discs have a thickness of about 1 millimeter or less, more preferably about 0.8 millimeters or less.

As discussed above, the discs used in the assay devices of the present invention preferably have a liquid-retention capacity, i.e., they retain an amount of a liquid deposited therein or thereon. At the low end, it may be preferred that each of the discs have a liquid-retention capacity of at least about 0.5 microliters, more preferably at least about 1 microliter, and even more preferably at least about 2 microliters. At the upper end, it may be preferred that each of the discs have a liquid retention capacity of about 100 microliters or less, or alternatively about 25 microliters or less. One preferred range of liquid-retention capacity for the discs may be about 1 microliter to about 20 microliters.

The number of discs on the assay device may vary depending on a variety of factors including sample size, disc size, etc. At the low end, it may be preferred that the device include at least about two or more discs, more preferably at least about 10 or more discs, and even more preferably about 25 or more discs. At the upper end, it may be preferred that the devices include about 10,000 discs or less, more preferably about 1,000 discs or less, and even more preferably about 600 discs or less. In other embodiments, it may be desirable to provide about 100 to about 200 discs on each assay device.

It may be preferred that all of the discs on the assay device be uniform in liquid-retention capacity. It may also be preferred that all of the discs also occupy the same surface area on the assay surface. By using discs that present uniform liquid retention capacity and size, the accuracy of both the culturing results and the detection of those results may be improved as compared to devices that present discs of different capacity and/or size.

Such a device with discs that are uniform in both liquid capacity and size may be particularly useful in the context of testing a liquid sample for microorganism concentration using MPN analysis. Certain regulatory requirements may dictate that a testing method must be able to detect one microorganism in a one-to-five-milliliter sample. Such a sample size is standard in the food processing industry for microbiological testing. Thus, for example, an assay device having 500 liquid-retaining discs, where each disc has a capacity of about 2 microliters, would be very useful for testing a 1-ml sample. A liquid-retaining disc having a capacity of 2 microliters may allow for rapid development of a detectable signal in accordance with the invention, and the use of about 400 to about 600 discs may provide a sufficiently large number of data points to substantially improve the confidence interval for an MPN analysis calculation. In addition, it is feasible to perform a manual count of liquid-retaining discs testing positive for the microorganism. Use of devices having substantially more than 400 liquid-retaining discs may require, as a practical matter, instrument-assisted or automated counting.

In an alternative embodiment, it may be desirable to provide discs of different liquid-retention capacity on the same device. In addition or in place of different capacity, it may be desirable to provide discs that occupy a different amount of surface area on the assay surface. In many instances, however, the discs with a different capacity will also occupy a different surface area on the assay surface.

It may further be preferred that the liquid retaining discs be provided in two or more sets, with each set including discs that are uniform in both liquid capacity and size. The capacities and sizes of the sets of discs are preferably different, and it may be further preferred that the capacities and sizes vary incrementally over the different sets of discs. For example, in one embodiment, the assay device may include one hundred discs in total, with fifty discs having a volume of about twenty microliters and fifty discs having a volume of about two microliters.

Figure 4:
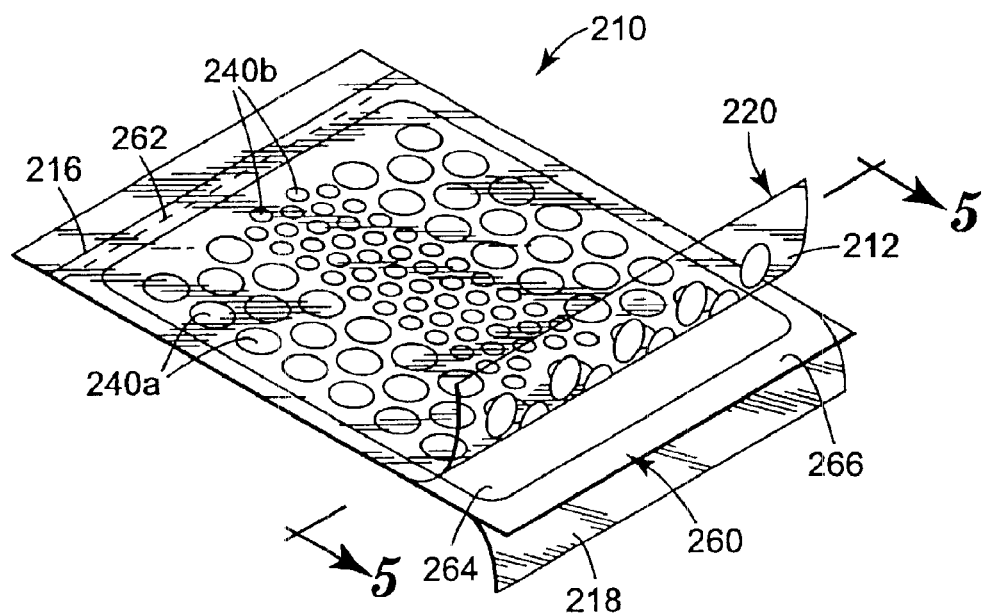
FIG. 4 is a perspective view of another assay device according to the present invention.
Figure 5:
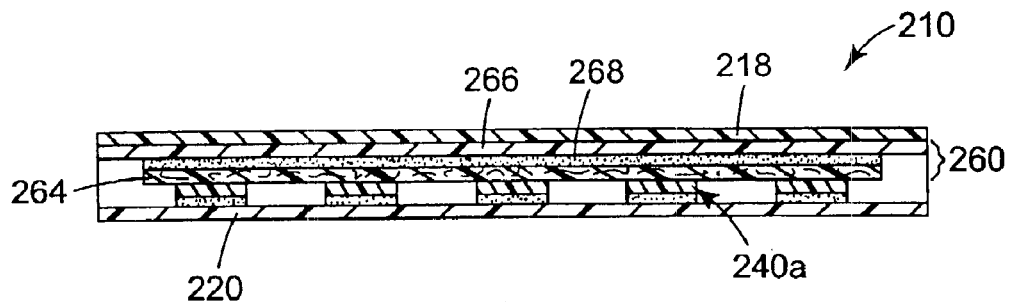
FIG. 5 is a cross-sectional view of the assay device of FIG. 4 taken along line 5—5 in FIG. 4.
Figure 6:
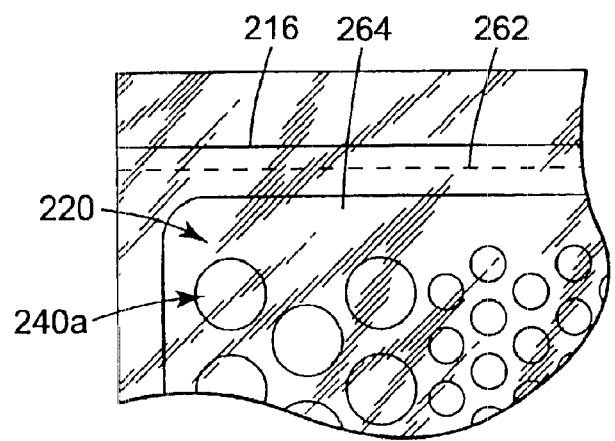
FIG. 6 is an enlarged plan view of a portion of the assay device of FIG. 4.

An assay device 210 is illustrated in FIGS. 4–6 that includes two sets of discs 240a and 240b that have different liquid retention capacities and different sizes. It may be preferred that the larger discs 240a substantially surround the smaller discs 240b, such as illustrated in FIG. 4. The larger discs 240a are generally located between the smaller discs 240b and the outer margin of the assay surface 212. Placement of the discs in this manner may reduce or prevent drying of the smaller discs 240b because the larger discs 240a may act to humidify the area of the smaller discs 240b, as well as partially shield smaller discs 240b from airflow that may dry the smaller discs 240b, such as may occur during elevated temperature incubation. To achieve this advantage, it may not be necessary that the larger discs 240a completely surround the smaller discs 240b, either with respect to the smaller discs 240b themselves or the outer margin of the assay surface 212.

The assay device 210 also includes an optional inoculation vehicle 260. The inoculation vehicle 260 is capable of retaining sample for subsequent inoculation of the discs 240a and 240b. Examples of possible inoculation vehicles 260 include, without limitation, absorbent pads, thermoformed plates, reservoirs, etc.

The inoculation vehicle 260 in the illustrated embodiment may preferably be attached to the assay device 210 in a manner to permit the vehicle 260 to come into contact with the discs 240a and 240b. One preferred method may be to attach the inoculation vehicle 260 along a perforation 262. In this configuration, the inoculation vehicle 260 may be removed from the device 210 after use simply by tearing along the perforation 262. The vehicle 260 preferably substantially covers the portion of the assay surface 212 on which the discs 240a and 240b are located.

To distribute the sample to the discs, the sample is first loaded into the inoculation vehicle 260. After loading the vehicle 260, it is placed in contact with the discs 240a and 240b. The sample preferably transfers from the vehicle 260 and into the discs 240a and 240b in a process that preferably occurs virtually simultaneously and uniformly.

In one embodiment, the inoculation vehicle 260 is an absorbent inoculation pad 264 with a backing 266 attached thereto. The pad 264 may be made of any number of materials, e.g., those listed above for the disc material. For manufacturing purposes, it may be desirable that the pad 264 be constructed of the same material as the discs 240a and 240b. The pad 264 may be any size or shape. Preferably, the pad 264 covers more of the assay surface 212 than that area in which the discs 240a and 240b are located such that the pad 264 covers all of the discs 240a and 240b to ensure that all of the discs are capable of being inoculated when the pad 264 is placed in contact with the discs 240a and 240b.

The backing 266 may be attached to the device 210 such that each device 210 preferably includes an inoculation vehicle 260 as delivered to a user. It may be preferred that the backing 266 be attached in a detachable manner, such as along a perforation 262. It may also be preferred that the backing 266 be relatively thin and that it not leach chemicals that may interfere with the growth or detection of target microorganisms. For manufacturing purposes, the backing 266 may be manufactured from the same material or materials as the substrate 220.

The pad 264 may be attached to the backing 266 in any number of ways known in the art, such as with adhesive 268. Preferably, the pad 264 and backing 266 are attached in a manner that does not result in leaching of chemicals.

Also illustrated in FIGS. 4–6 is an optional coversheet 218 that may be provided with the assay device 210. The coversheet 218 may serve to protect the discs 240a and 240b from contamination or desiccation once sample has been added to the device 210. The coversheet 218 may be constructed of any number of materials. It may be preferred that the coversheet 218 have one or more of the following properties: flexibility, transparency to the extent one may conduct excitation and/or detection through the coversheet 218, compatibility with growing microorganisms and the excitation and/or detection system to be used with the device (e.g. does not exhibit luminescence or fluorescence, or opacity to the degree that would substantially interfere with detection), and chemical stability (i.e., does not leach undesirable chemicals upon coming into contact with liquid sample), etc.

The coversheet 218 may be attached to the device 210 in such as way that it covers substantially all of the discs 240a and 240b, more preferably all of the discs 240a and 240b. It may be preferred that the coversheet 218 and the assay surface 212 are sized to permit the coversheet 218 to contact and seal to the assay surface 212 in use. For purposes of this application, to "seal" does not require that the connection between the assay surface 212 and coversheet 218 be airtight. Instead, coversheet 218 may merely overlay and come into substantial contact with the substrate 212 to reduce or prevent contamination during use and excessive evaporation from the discs 240a and 240b.

In one embodiment, the coversheet 218, substrate 220, and inoculation vehicle 260 may all be attached to each other at one end of the 210 device to form a hinge 216. In this configuration, the inoculation vehicle 260 may preferably be attached between the coversheet 218 and the substrate 220.

In other embodiments, a coversheet 218 may be added to the assay device 210 after inoculation of the discs 240a and 240b. The coversheet 218 may be attached by any suitable technique, e.g., adhesives, etc.

The discs used in the assay devices of the present invention may include a variety of assay reagents to assist in growth, detection, and/or enumeration of selected microorganisms. One assay reagent is nutrient growth media which may be provided as a coating or other deposition within or on the liquid-retaining discs, in amounts sufficient to achieve desired concentrations when a liquid test sample is distributed into the discs. It may be preferred that the growth media exhibit selectivity for certain groups of microorganisms whose growth is permitted or differentiated by the growth media.

The nutrient growth media may be provided, for example, by placing or distributing a solution or suspension of the nutrient medium onto the discs and drying to produce a coating or deposition of the nutrient medium on the discs. Alternatively, components of the growth media may be present in the adhesive or other substance that attaches the discs to the substrate (if applicable). Regardless of its exact location before inoculation of the discs, the growth media is preferably provided in a manner such that it ultimately diffuses into the disc material to provide for growth of the target microorganisms (if present).

The discs of the assay devices of the present invention may also include other assay reagents on or in the discs. Such assay reagents may include, without limitation, gelling agents, indicator substances, etc. A gelling agent may assist in "encapsulating" the growing microorganisms. Such gelling agents are known to those of skill in the art, and include any water-absorbing material that becomes a gel upon addition of an aqueous liquid.

Indicator substances useful in connection with the invention may include any substance that produces a signal in the presence of the growing microorganism. Examples of some indicator substances include, but are not limited to chromogenic, fluorescent, fluorogenic, luminescent, electrochemical and other indicators.

In the present invention, fluorogenic indicator substances may be preferred because they may be detected at relatively low concentrations. Suitable fluorogenic indicator substances may include, without limitation, 4-methylumbelliferyl phosphate, and 4-methylumbelleferyl-beta-D-glucopyranoside, L-phenylalanine-7-amido-4-methylcoumarin. Others may include 4-methylumbelliferyl acetate and 4-methylumbelliferyl sulfate.

The assay reagents can be immobilized in the discs by any of numerous methods for immobilizing assay reagents on solid substrates known to those of skill in the art. Such methods may include, for example, drying down assay reagent-containing liquids in the discs, as well as other methods for noncovalently attaching biomolecules and other assay reagents to a solid substrate. Alternatively, various methods may be employed to covalently attach assay reagents to the discs by methods well known to those of skill in the art. An advantage of the present invention is that soluble assay reagents can be used, since diffusion is preferably reduced or prevented by confinement of the aqueous biological sample liquid in the liquid-retaining discs.

The liquid test samples used in connection with the assay devices and methods of the present invention may be any sample of interest, from any source. The sample may be distributed to the liquid-retaining discs directly, or the sample may be diluted before distribution to the discs. The determination as to whether sample dilution is necessary will depend on a variety of factors such as sample source and age, and such determination is a routine matter to those of skill in the art.

As an alternative to providing the desired assay reagents in the discs before inoculation, it may be preferred to include one or more of the desired assay reagents, e.g., a growth media, indicator substance, gelling agent, etc., in the liquid test sample itself.

Various methods may be employed to distribute a liquid test sample to the liquid-retaining discs. More than one method may be applicable to a particular device, although the preferred method may depend to some extent on the configuration of a particular assay device. The sample may be poured or pipetted over the device and the sample spread to the liquid-retaining discs by tilting or rocking the device. Alternatively, the assay device or a portion of the assay device can be immersed in the sample. Upon removal from the liquid sample, liquid may be retained in hydrophilic liquid-retaining discs and substantially excluded from a hydrophobic land area between the discs.

After the sample is distributed to the hydrophilic liquid-retaining discs of the assay device, various assays may be carried out depending on desired uses. For microbial detection or enumeration, the assay device may be incubated for a time sufficient to permit at least one cell division cycle of the microorganism. For these purposes, the device is generally incubated at about 25° C. to about 45° C., more preferably at about 30° C. to about 37° C. The incubation time for microbial detection will vary. The detection time will also vary depending on the growth rate and the number of microorganisms present in the sample. Taking into account these considerations, detection time for purposes of enumeration may be as little as about 10 hours. This relatively short incubation time represents a distinct advantage over detection methods currently used, which typically require incubation times of about 24 hours or more.

Following incubation of the assay device, the presence or absence of microorganisms in discs (and thus in the liquid test sample) is detected. The mode of detection depends on the type of indicator substance used in the method. Any indicator substance that is capable of providing a detectable signal may be used. Such indicators include but are not limited to fluorescent, chromogenic, luminescent, and electrochemical indicators. The presence or absence of a microorganism in a disc can be visually detected, with the naked eye or microscopically, if a chromogenic or luminescent indicator is used. The indicator may be coated or otherwise incorporated into the discs.

It may be preferred that the mode of detection include the emission of electromagnetic signal energy that can be reflected by the metallic layer included in the devices of the present invention. It may also or alternatively be preferred that the mode of detection rely on excitation by electromagnetic energy that is blocked from reaching the underlying substrate (and more preferably reflected) by the metallic layer included in the assay devices of the invention.

If a fluorescent indicator substance is used, equipment and methods for detecting a fluorescent signal may be employed for detection. There are numerous indicator substances and signal detection systems, including systems for detecting electrochemical changes, known in the art for detecting microorganisms, and any such substance or system may be used in accordance with the present invention.

The detection of microorganisms in the liquid sample may further involve the enumeration of a microorganism count in the liquid test sample. In a preferred embodiment, the enumeration is performed using MPN. Once the number of liquid-retaining discs containing the microorganism of interest is determined, an MPN calculation can be made using known MPN techniques. If desired, the number of microorganisms in an individual disc can then be determined using known techniques, for example, signal intensity compared to a known standard, or by plating the contents of the disc. Advantageously, the large number of liquid-retaining discs that may be used in the method of the invention allows for narrower intervals (e.g., in comparison to the standard 3-tube or 10-tube MPN methods) for the 95% confidence limits in an MPN analysis of a liquid test sample.

Because of the large number of liquid-retaining discs that may be manufactured in a single device, it is possible to use a single device in the detection and enumeration of multiple microorganisms of interest, while retaining the advantages of the invention. For example, a single liquid test sample can be tested for the presence or concentration of *E. coli* and *S. aureus*. One portion of an assay device can contain discs for the detection and enumeration of one of these microorganisms, while a second set of discs can be directed to detection and enumeration of another microorganism of interest. This is accomplished, for example, by including microorganism-specific nutrients and/or indicator substances in the respective sets of liquid-retaining discs. Alternatively, all liquid-retaining discs can contain assay reagents designed for the simultaneous detection of multiple microorganisms. For example, *E. coli* can be detected with a fluorescent indicator substance while, at the same time, other coliforms are detected with, e.g., a chromogenic or other indicator substance.

Subsequent tests may be conducted. For example, the discs can be removed from the device and transferred into a test tube to differentiate the specific microorganisms growing thereon.

In another embodiment, aliquots of the liquid test sample can be distributed to a plurality of liquid-retaining discs of an assay device, wherein the assay device includes a plurality of sets of discs. Each set has discs of uniform size, and the device has at least two sets of discs. For example, the assay device can include a plurality of lanes, with the liquid-retaining discs in a particular lane having the same liquid-retention capacities. This feature allows for the distribution of the liquid test sample into different test volume sizes within a single assay device. In MPN, this feature provides a significant advantage in that, for a highly concentrated sample, an appropriate volume size may be selected and MPN analysis performed using a single distribution step in a single device without the need for serial dilutions.

Figure 7:
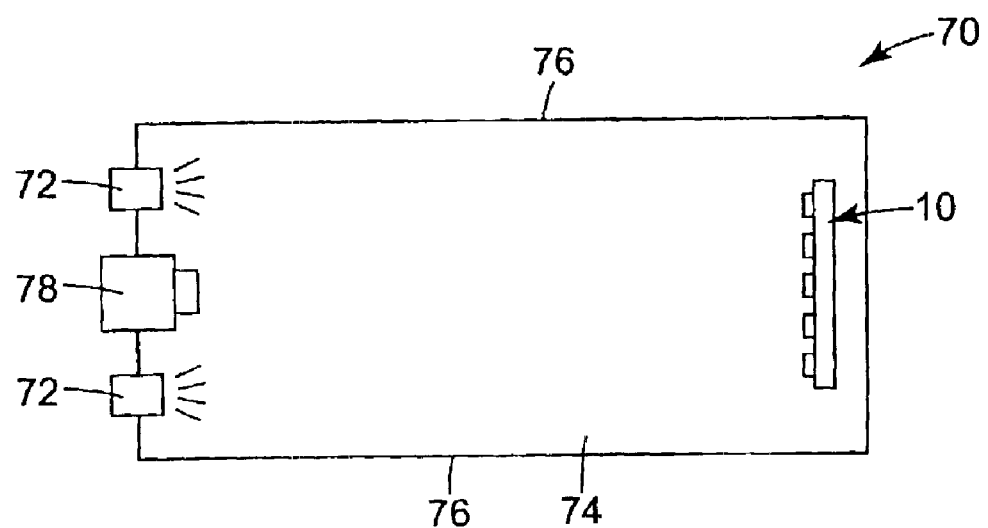
FIG. 7 is a schematic diagram of an excitation/detection system useful with the assay devices and methods of the present invention.

FIG. 7 is a schematic depiction of one system that may be used in connection with detecting and/or enumerating selected microorganisms present in the discs on the assay devices described above. It should be understood that the system may also be used with other assay devices as well—its use and advantages are not necessarily limited to the use of reflective disc assay devices as are described above.

The system 70 includes at least one excitation source 72, more preferably two or more sources 72 that supply the electromagnetic excitation energy of selected wavelengths to an assay device 10 located within the detection chamber 74. The detection chamber 74 is largely defined by at least one wall 76 that, in one form, may be provided in the shape of a right circular cylinder. If the detection chamber 74 is not cylindrical in shape, it may include a plurality of walls.

The excitation source 72 may take any suitable form, provided the source 72 emits sufficient energy in the excitation wavelengths required for the assay device 10 being processed. For example, the source 72 may emit ultraviolet light having a wavelength of 365 nanometers which may be useful for a number of fluorogenic indicator substances. The excitation source 72 may produce coherent or non-coherent electromagentic radiation.

The system 70 also includes a detector 78 arranged to detect electromagnetic signal energy emitted from the assay device 10 in response to the electromagnetic excitation energy. The detector 78 may be provided by any suitable device or devices capable of detecting the electromagnetic signal energy, including, but not limited to a CCD camera, photodiodes, etc.

The wall 76 of the detection chamber 74 is constructed of materials that reflect a significant portion of the electromagnetic excitation energy incident thereon. By reflecting the excitation energy instead of absorbing or transmitting it, the amount of energy reaching the assay device may be increased. Another advantage is that the reflections may result in improved uniformity in the intensity of the excitation. It may be preferred that the wall 76 reflect at least about 80% (even more preferably at least about 90%) of the electromagnetic excitation energy incident thereon (where the energy is incident on the wall along an axis normal to the wall surface). In some instances it may be desirable that the wall 76 not reflect the electromagnetic signal energy to avoid reflections of such energy from reaching the detector 78. Such energy may, instead be absorbed or transmitted out of the detection chamber 74.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of this invention, and it should be understood that this invention is not limited to the illustrative embodiments set forth herein. Accordingly, the invention is to be limited only by the claims provided below.

EXAMPLES

The following examples are offered to aid in understanding of the present invention and are not to be construed as limiting the scope thereof. Unless otherwise indicated, all parts and percentages are by weight.

Example 1
Disc Devices with Vapor-Coated Metal Surface

Absorbent disc assay devices having a vapor-coated metal surface and capable of being used for the detection and enumeration of microorganisms in a liquid test sample were constructed as described in this example.

A sheet of absorbent nonwoven cellulosic material (Product Grade 903, 0.52-mm thick, 179 g/m$^2$, Schleicher and Schuell, Keene, N.H.) was laminated to a polyester film (Rexam "D" Liner, Rexam Release, West Chicago, Ill.) with an isooctyl acrylate/acrylamide (96/4 weight ratio) pressure sensitive adhesive (PSA). Circular discs (8-mm in diameter) were then cut into the dried laminate using a controlled depth die that cut only through the nonwoven material and adhesive layers. The non-disc material was then removed from the laminate and discarded. Forty discs were carefully peeled from the film with forceps and transferred to a 105-mm×115-mm sheet of 2-mil (0.05-mm) thick polyester film (Grade NAT 2.0 PET Silox H6G/0, Akrosil International Paper, Purchase, N.Y.) to form an 8×5 array of circular discs with approximately 3–5 mm between discs.

A 105-mm×115-mm sheet of biaxially-oriented polypropylene film (0.04-mm thick, 3M Co.) was then adhered with double stick tape to the disc-side edge of the bottom sheet to serve as a coversheet for the device. The device was placed on a flat counter and a wallpaper roller was rolled over the closed coversheet to press the discs against the bottom sheet. The resulting Disc Device 1A, a comparative device having no vapor-coated metal surface, was used for fluorescent signal evaluations in Example 2.

Another disc device was prepared as described for Disc Device 1A, except that in place of the Grade NAT 2.0 PET Silox polyester film was substituted 7-mil (0.18-mm) thick polyester film (3M Co., St. Paul, Minn.) that was vapor coated with an estimated 70 to 150 nm of aluminum metal on the side to which the discs were adhered. The resulting device, designated Disc Device 1B and having a vapor coated metal surface, was compared with Disc Device 1A in Example 2.

Disc assay devices for use in the detection of microorganisms were constructed as follows. A sheet of absorbent nonwoven cellulosic material (Dexter Grade 10201, 0.415-mm thick, 48.5 g/m$^2$ Dexter Nonwovens, Winsor Locks, Conn.) was laminated to a polyester film (Rexam "D" Liner) as described above, except that the material was saturated with an aqueous broth containing the growth nutrients and indicator chemicals listed in Table 1 and dried prior to lamination. Circular discs (8-mm in diameter) were then cut into the dried laminate using a controlled depth die that cut only through the nonwoven material and adhesive layers. The non-disc material was then removed from the laminate and discarded. Sterile forceps were then used to peel 15 discs from the device and the discs were transferred to a 105-mm×115-mm bottom sheet of polyester film (0.12-mm thick, 3M Co., St. Paul, Minn.) in a 3 by 5 spatial pattern with approximately 1 cm between discs. A 105-mm×115-mm sheet of biaxially-oriented polypropylene film (0.04-mm thick, 3M Co.) was then adhered with double stick tape to the disc-side edge of the bottom sheet to serve as a coversheet for the device. The device was placed on a flat counter and a wallpaper roller was rolled over the closed coversheet to press the discs against the bottom sheet.

The resulting device, a comparative device having no vapor-coated metal surface, was designated Disc Device 1C and was used for the detection of bacteria as described in Example 3. Another disc device was prepared as described for Disc Device 1C, except that in place of the 0.12-mm thick polyester film was substituted 7-mil (0.18-mm) thick polyester film (3M Co.) that was vapor coated with aluminum metal as described above on the side to which the discs were adhered. The resulting device, designated Disc Device 1D and having a vapor coated metal surface, was compared with Disc Device 1C in Example 3. Both Disc Devices 1C and 1D were gamma irradiated to a level of about 10 kGy before use in Example 3.

TABLE 1

| Component | Concentration (g/l) |
|---|---|
| Sodium Pyruvate (Sigma Chemical Co., St. Louis, MO) | 4.4 |
| Tryptone (Difco Laboratories, Detroit, MI) | 7.5 |
| Yeast Extract (Difco Laboratories) | 2.5 |
| Glucose (Difco Laboratories) | 3.6 |
| $KH_2PO_4$ (Fisher Chemicals, Fair Lawn, NJ) | 1.08 |
| $Na_2HPO_4$ (Fisher Chemicals) | 5.97 |
| $MgSO_4.7H_2O$ (Aldrich Chemical Co., Milwaukee, WI) | 0.98 |
| 4-Methylumbelliferylphosphate (Biosynth Int., Naperville, IL) | 0.05 |
| L-Alanine-7-amido-4-methylcoumarin (Biosynth Int.) | 0.05 |
| L-Phenylalanine-7-amido-4-methylcoumarin (Biosynth Int.) | 0.05 |

Example 2

Measurement of Fluorescent Signal from Disc Devices

The objective of this example was to measure and compare the intensity of fluorescent signals emitted from a fluorescent compound present in the nonwoven material of Disc Devices 1A and 1B.

To each of the nonwoven discs of Disc Device 1A (without a metal surface) and Disc Device 1B (having a metal surface), after carefully lifting the top film, was added 15 microliters of a solution that contained from 0 to 500 mmoles/ml of 4-methylumbilliferone. The top film was then gently lowered to close the devices. (It is noted that 4-methylumbilliferone is the end product of the reaction of, for example, 4-umbelliferyl phosphate, and the microbial enzyme phosphatase. This reaction is useful to detect the presence of bacteria as 4-methylumbilliferone fluoresces under ultraviolet light.)

Four measurements per device were taken at each concentration of 4-methylumbilliferone with a custom-designed fluorescence detector. The CCD camera aperture was constant for all measurements, and exposure times were 10, 20, 40, and 60 msec. The raw images were analyzed using Adobe Photoshop v.5.0 image analyses software (Adobe Systems, Inc., San Jose, Calif.). The elliptical marquee tool, with a constrained aspect ratio, was used to select an area within each disc that approximated at least 70–80% of the disc image. The average pixel fluorescence was determined within the selected area and the results, in relative fluorescence units (RFU) are reported in Table 2.

The custom-designed fluorescence detector consisted of a CCD camera (constructed with a black and white CCD chip, Product No. ICX084AK, Sony Corp., Japan), ultraviolet illumination (365 nm), reflective walls, and a flat surface that could hold a disc device. The camera was positioned to face the discs at a distance of approximately 20 cm and a 1-mm thick filter (GG420, Schott Glas, Germany) was placed in front of the camera. The discs were illuminated by two ultraviolet lamps (Product No. BF3160UV1, JKL Co., Pacoima, Calif.) placed on either side of the camera. A 1-mm thick filter (UG11, Schott Glas) was placed in front of the lamps. The walls of the detector were reflective to help provide more uniform illumination of the discs. When fluorescence occurred, the camera detected the resultant visible light.

TABLE 2

| 4-Methylumbilliferone (mmoles/ml) | Disc Device 1A (No Metal Surface) | | Disc Device 1B (Metal Surface) | |
|---|---|---|---|---|
| | Signal (RFU) | Signal/Background | Signal (RFU) | Signal/Background |
| 0 | 51.5 | 1.0 | 32.3 | 1.0 |
| 25 | 52.3 | 1.0 | 38.3 | 1.2 |
| 50 | 53.5 | 1.0 | 41.3 | 1.3 |
| 100 | 56.5 | 1.1 | 50.3 | 1.6 |
| 250 | 65.3 | 1.3 | 73.7 | 2.3 |
| 500 | 77.5 | 1.5 | 101.7 | 3.1 |

The data in Table 2 show that the Disc Device 1A (without a vapor-coated metal surface) produced a higher level of "background" fluorescence than Disc Device 1B (having a vapor-coated metal surface) (51.5 RFU vs. 32.3 RFU at 0 mmoles/ml 4-methylumbilliferone). The data also show that Disc Device B produced a higher signal to background ratio than Disc Device A at all levels of 4-methylumbilliferone concentration. For example, at 500 mmoles/ml of 4-methylumbilliferone, the signal/background level of Disc Device B was 3.1 vs. 1.5 for Disc Device A. It is concluded that the use of a disc device with a vapor-coated metal surface offers the advantages of both reduced background fluorescence and increased fluorescent signal to background levels.

EXAMPLE 3

Detection of Bacteria with Disc Devices

The objective of this example was to measure and compare the intensity of fluorescent signals emitted from growing *E. coli* bacteria present in the nonwoven material of Disc Device 1C (without a metal surface) and Disc Device 1D (having a metal surface).

An overnight culture of *E. coli* bacteria [(QC strain P6), grown overnight in tryptic soy broth (Remel, Inc., Lenexa, Kans.)] was diluted into Butterfield's phosphate buffer (Hardy Diagnostics, Santa Maria, Calif.) to obtain dilution factors of $10^{-3}$, $10^{-4}$, $10^{-5}$, and $10^{-6}$. Sterile Butterfield's phosphate buffer was used as a negative control. These dilution factors correspond to cell densities of approximately $10^5$, $10^4$, $10^3$, and $10^2$ colony forming units per ml, respectively.

The top film of Disc Devices 1C and 1D (2 replicates/device) were carefully lifted and each disc of each device was inoculated with 15 microliters of each dilution (3 replications each) or the negative control solution (3 replications). The top film was gently lowered to close the devices and they were enclosed in "GLADLOCK ZIPPER" storage bags (First Brands Corporation, Danbury, Conn.) each containing a paper towel moistened with water. The sealed bags were placed in an incubator at 35° C. After 24 hours incubation, the fluorescent images of the devices were obtained using the custom-designed detector as described in Example 2. An exposure time of 5 milliseconds was used and the aperture of the CCD camera remained constant for all of the images.

The raw images from the detector were analyzed using Adobe Photoshop v.5.0 image analyses software as described in Example 2, and the resulting data are shown in Table 3.

TABLE 3

| E. coli Dilution | Disc Device 1C (No Metal Surface) | | Disc Device 1D (Metal Surface) | |
|---|---|---|---|---|
| | Signal (RFU) | Signal/ Background | Signal (RFU) | Signal/ Background |
| Control (no E. coli) | 40 | 1.0 | 36 | 1.0 |
| $10^{-3}$ | 126 | 3.1 | 197 | 5.4 |
| $10^{-4}$ | 122 | 3.0 | 210 | 5.8 |
| $10^{-5}$ | 122 | 3.0 | 208 | 5.7 |
| $10^{-6}$ | 107 | 2.7 | 190 | 5.2 |

The data in Table 3 show that Disc Device 1D (having a vapor-coated metal surface) produced a higher signal to background ratio than Disc Device 1C (without a vapor-coated metal surface) at all dilution levels. For example, at a dilution factor of $10^{-3}$, the signal/background level of Disc Device D was 5.4 vs. 3.1 for Disc Device C. The data also show that the signal RFU for each device was essentially not dependent on the *E. coli* dilution. This result is explained by the 24-hour growth period, after which all of the discs would have contained approximately the same number of bacteria. From this example, it is concluded that the use of a disc device with a vapor-coated metal surface offers the advantage of increased fluorescent signal to background levels.

What is claimed is:

1. A method of detecting at least one target microorganism comprising:
    providing a disc assay device comprising a substrate; a plurality of liquid-retaining discs attached to the substrate, each of the plurality of discs comprising first and second opposing surfaces; and a reflector proximate the first surface of each of the plurality of discs; and wherein at least one of the discs further comprises growth media, an indicator substance, and a target microorganism;
    directing excitation energy at the disc assay device; and
    detecting signal energy emitted from each of the plurality of discs comprising the target microorganism in response to the excitation energy; wherein at least a portion of the signal energy is reflected by the reflector.

2. The method of claim 1, wherein substantially all of the excitation energy that passes through each of the plurality of discs is reflected by the reflector proximate the first surface of each of the plurality of discs.

3. The method of claim 1, wherein the substrate reflects electromagnetic energy of the selected wavelengths, and further wherein the reflector proximate the first surface of each of the plurality of discs comprises the substrate.

4. The method of claim 1, wherein the reflector proximate the first surface of each of the plurality of discs comprises a reflective layer located between each of the plurality of discs and the substrate.

5. The method of claim 1, wherein the substrate comprises a substrate surface and the reflector proximate the first surface of each of the plurality of discs comprises a reflective layer located between each of the plurality of discs and the substrate surface, and further wherein the reflective layer is substantially coextensive with the substrate surface.

6. The method of claim 1, wherein the reflector proximate the first surface of each of the plurality of discs comprises a metallic layer located between each of the plurality of discs and the substrate.

7. The method of claim 1, wherein the substrate comprises a substrate surface and the reflector proximate the first surface of each of the plurality of discs comprises a metallic layer located between each of the plurality of discs and the substrate surface, and further wherein the metallic layer is substantially coextensive with the substrate surface.

8. The method of claim 1, wherein each of the plurality of discs comprises fibrous material.

9. The method of claim 1, further comprising:
    contacting the plurality of discs with a liquid sample comprising the target microorganism, wherein at least a portion of the liquid sample is retained within at least one of the plurality of discs; and
    incubating the retained liquid sample.

* * * * *